United States Patent [19]

Heckele

[11] Patent Number: 4,881,523
[45] Date of Patent: Nov. 21, 1989

[54] ENDOSCOPE

[75] Inventor: Helmut Heckele, Knittlingen, Fed. Rep. of Germany

[73] Assignee: Richard Wolf GmbH, Fed. Rep. of Germany

[21] Appl. No.: 305,165

[22] Filed: Feb. 2, 1989

[30] Foreign Application Priority Data

Feb. 4, 1988 [DE] Fed. Rep. of Germany ....... 3803212

[51] Int. Cl.$^4$ ................................................. A61B 1/12
[52] U.S. Cl. ......................................................... 128/4
[58] Field of Search ......................................... 128/4, 6

[56] References Cited

U.S. PATENT DOCUMENTS

| | | | |
|---|---|---|---|
| 4,261,343 | 4/1981 | Ouchi et al. | 128/4 |
| 4,517,962 | 5/1985 | Heckele | 128/6 |
| 4,537,209 | 8/1985 | Sasa | 128/4 X |
| 4,694,821 | 9/1987 | Kondo | 128/4 |

Primary Examiner—William H. Grieb
Attorney, Agent, or Firm—Hill, Van Santen, Steadman & Simpson

[57] ABSTRACT

An endoscope for endonasal surgery in particular, comprises a suction and flushing shaft accommodating an optical system and having a suction channel and a flushing channel. A switching valve is accommodated in a handle of the endoscope, for connecting the suction channel and the flushing channel to a suction source and to a flushing fluid source, respectively. The switching valve allows the suction channel to be flushed clear of bodily tissue or secretions, for example, during use of the endoscope within a bodily cavity. To this end, the switching valve is such that the suction channel can be cleansed by flushing fluid in an intermediate position of the switching valve, whilst the suction channel is shut off from the suction source.

10 Claims, 2 Drawing Sheets

ENDOSCOPE

FIELD OF THE INVENTION

This invention relates to an endoscope and concerns, especially, an endoscope for endonasal surgery, the endoscope comprising a suction and flushing shaft and a flushing channel, a handle adapted to be coupled to the shaft and a change-over or switching valve accommodated in the handle and having switching positions for connecting the suction channel and the flushing channel to a suction source and to a flushing fluid source, respectively, and for interrupting the connections.

BACKGROUND OF THE INVENTION

There is disclosed in DE-U-81 36 066 an endoscope for endonasal surgery, which has a suction and flushing shaft accommodating an optical system and a handle for releasable connection to said shaft. A valve is accommodated in the handle, by means of which valve the suction channel can be shut off by operating the valve and the flushing channel opened for infeeding a flushing fluid. The construction of the valve is such that the suction, or vacuum channel cannot be cleansed during use of the endoscope, which may for example be necessary if such channel is partly or wholly blocked by bodily secretions, pieces of tissue or the like, whereby use of the endoscope is at least restricted or is even wholly prevented. In such case the endoscopic examination must be suspended and the clogged shaft replaced by another shaft. Since the cleansing of such shafts is not usually carried out at the site of use, that is to say not immediately but at a later time, the suction channel must not only be subjected to normal disinfection or sterilisation but must also be mechanically cleaned in order to remove hardened or encrusted material therefrom. Also, the handle is so shaped that it needs to be fully enclosed by the hand in order to use the endoscope.

SUMMARY OF THE INVENTION

The invention primarily concerns the problem of providing means for flushing the vacuum channel clear, for the elimination of impurities during the use of the endoscope without impairing the suction and flushing functions and without having to remove the endoscope from its place of application in a body cavity, in order to replace the soiled suction and flushing shaft by a sterile suction and flushing shaft and to cleanse the soiled shaft mechanically as well as to disinfect and/or sterilise it. A further problem with which the invention is concerned is the formation of the handle in such a way as to allow the endoscope to be handled without fatigue.

According to the invention, the switching valve has a switching position, which may be an intermediate position, in which the suction channel is connected to the flushing fluid source. Thus, the suction channel can be cleansed by reverse flow of the flushing fluid therethrough in order to remove bodily secretions, pieces of tissue, or the like adhering to the interior of the suction channel and thereby reducing or wholly blocking its cross-section. Said reverse flow is performed for brief periods in each case, by repeated actuation of the switching valve. To this end, the switching valve may be constructed so that whilst the suction channel is connected to the flushing fluid source, the connection between the flushing channel and that source, as well as the connection between the suction channel and the suction source are interrupted, and so that in an inoperative switching position of the switching valve, the suction channel is connected to the suction source and the flushing channel is shut off from the suction source, the switching valve having a switched through switching position in which the flushing channel is connected to the flushing fluid source and the suction channel is shut off from the suction source.

For ease of handling, the switching valve may be retained in said inoperative switching position by means of a spring and said intermediate position may be defined by detent means adapted to be overridden by the spring.

For handling the endoscope without fatigue, the handle is preferably provided with at least two gripping holes separated from each other by a web, at least one of these holes being dimensioned to receive a finger.

DETAILED DESCRIPTION OF THE INVENTION

Figure 1:
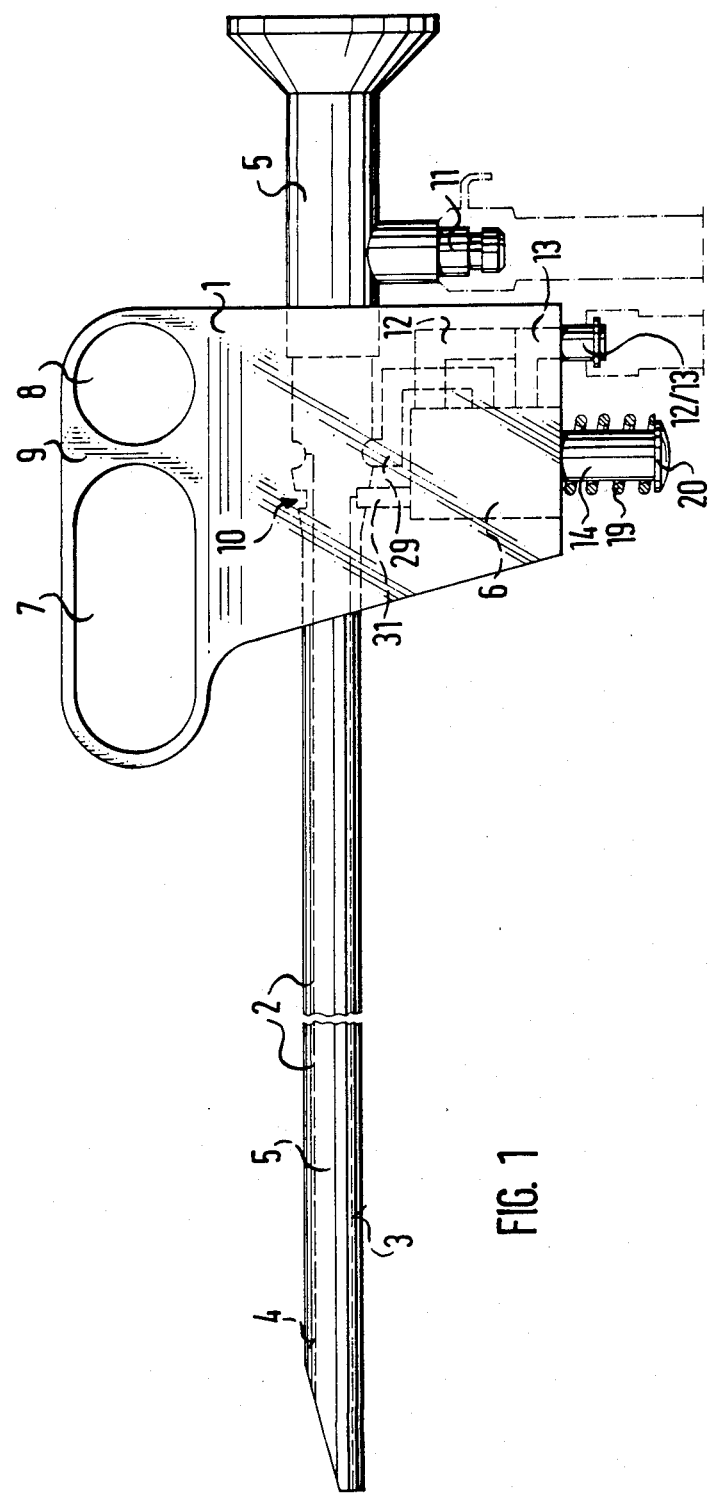
FIG. 1 shows a side view of an endoscope for endonasal surgery.
Figure 4:
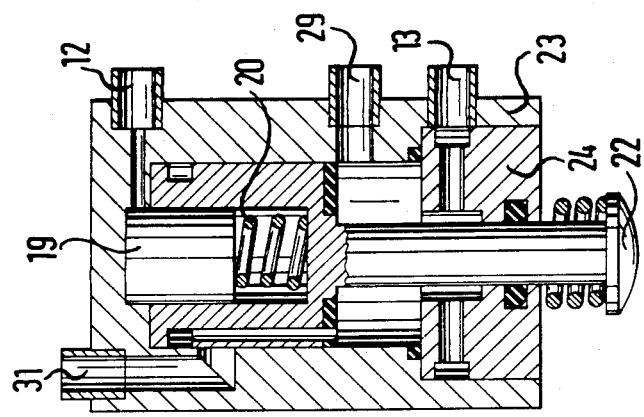
FIG. 4 is a cross-sectional view through the switching valve in a switched through switching position.
Figure 2:
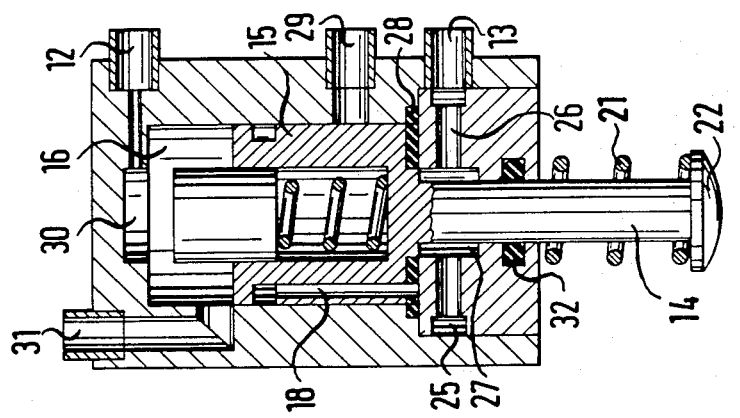
FIG. 2 is a cross-sectional view through a switching valve of the endoscope, in an inoperative switching position.

As shown in FIG. 1 the endoscope substantially comprises a handle 1, a suction and flushing shaft 2 having a suction channel 3 and a flushing channel 4, to which shaft the handle 1 is adapted to be coupled, an eyepiece of an optical system 5 at the proximal end of the endoscope, and a switching valve 6. The handle 1 is provided with two finger holes 7 and 8, separated by a web 9, through which several fingers can be inserted in order to hold the endoscope. The web 9 may be omitted, so that a single hole is provided through which both the fingers and the palm of the hand can be inserted. The web 9, however, provides for better handling of the endoscope in particular during actuation of the switching valve 6. If the web 9 is gripped between two fingers more securely to hold the endoscope, the valve actuating force, which is directed transversely of the longitudinal axis of the endoscope will not impair the positioning of the endoscope for examination of the area selected. The vacuum and flushing shaft 2 is releasably secured in a known manner in a seat 10 which is coupled to the shaft 2 by means, for example, of a ball detent. A light transmitting cable connector 11 is provided in the area of the eyepiece of the optical system 5. The handle 1 comprises a suction connector 12 and a flushing connector 13 for releasable connection to vacuum and flushing hoses (not shown). A gap is provided between the connector 11 and the handle 1, the optical system 5 extending through the shaft 2 and the proximal-side of the handle 1. This allows ready coupling of a light transmitting cable to the connector 11 and the suction and flushing shaft 2 to be turned about the longitudinal axis of the endoscope, if needed, together with the optical system 5. The switching valve 6 is in the lower part of the handle 1 and is operated by means of a pressure-actuated plunger 14 connected to a piston 15 in a cylinder 16 (FIGS. 2 and 4).

Near its leading end, the piston 15 is formed with a peripheral annular channel 17 which communicates by way of one or more axial bores 18 in the piston 15, with the trailing end face of the piston 15. The piston 15 also has an internal piston 19 bearing against a compression spring 20. In the inoperative swiching position of the switching valve 6, the pressure-actuated plunger 14 is retained in a retracted position (FIG. 2) by means of a spring 21 acting between the head 22 of the plunger 14 and the casing 23 of the valve 6.

The cylinder 16 is closed at one end by a closure plate 24 which locates the plunger 14 and into which the flushing connector 13 opens. The connector 13 is joined to an annular channel 25 which is placed in communication by way of one or more radially extending channels 26 with an annular channel 27 encircling the plunger 14, which channel opens into the cylinder 16. To prevent accidental and uncontrolled ingress of flushing fluid in the channels 25, 26 and 27, into the cylinder 16, a sealing element 28 is provided either at the upper end of the closure plate 24 or on the end face of the piston 15 facing the plate 24. A connector pipe 29 which is directly connected to the flushing channel 4 in the shaft 2, communicates to an increasing extent with the cylinder 16 as the piston 15 is advanced. The suction connector 12 leads into a stepped part 30 of the cylinder 16, into which part 30, the internal piston 19 is sealingly engageably upon advance of the piston 15. A connector pipe 31 is also provided by way of which the suction channel 3 in the shaft 2 is connected to part of the cylinder 16 which is ahead of the piston 15 in its retracted position.

The endoscope is readily operable by virtue of the structural arrangement of the switching valve 6. Bodily secretions and the like can be drawn off by suction in the inoperative position (FIG. 2) of the valve 6, such secretions being liable to be drawn off by suction by way of the suction channel 3 present in the shaft 2, the cylinder 16, 30 and the vacuum connector 12.

Figure 3:
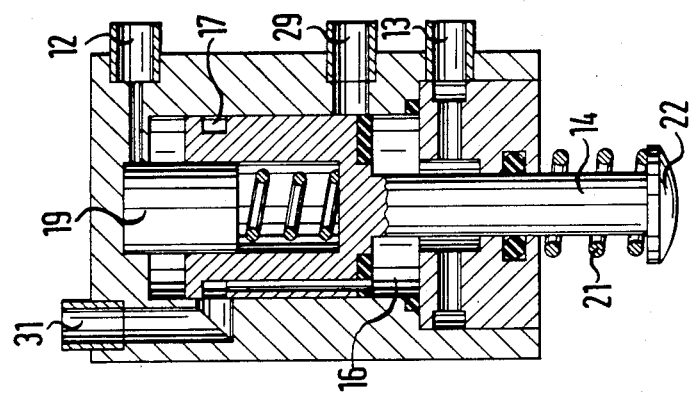
FIG. 3 is a cross-sectional view through the switching valve in an intermediate switching position.

If the switching valve 6 is operated by advancing the plunger 14 against the action of its spring 21 so as to advance the piston 15 in its cylinder 16, as far as the intermediate (FIG. 3) position which may be defined by detent means (not shown), the communication of the suction connector 12 with the cylinder 16 is cut off by the engagement of the piston 19 in the stepped part 30 of the cylinder 16 and, flushing fluid fed in by way of the channels 25, 26 and 27 is supplied by way of the axial bores 18, the annular channel 17 and the connector pipe 31, to the suction channel 3 in the shaft 2. There is accordingly a reverse flow of flushing fluid along the channel 3 under positive pressure, in said intermediate position of the valve 6, thereby efficiently to cleanse the channel 3. This flushing operation is performed briefly in each case during use of the endoscope, to prevent adhesion of bodily secretions, pieces of tissue or the like in the suction channel 3 or to free and/or remove substances which already adhere therein so as to reduce or clog the cross-section of the channel 3. Since the quantity of flushing fluid used for the purpose is comparatively small, it is unnecessary to withdraw said fluid by suction, following the cleansing operation. The quantity of flushing fluid that is fed into the suction channel 3 for scavenging it, depends upon the time during which the piston 15 is retained in its intermediate position.

If the piston 15 is advanced to its (FIG. 4) switched through position, beyond said intermediate position, the piston 15 shuts off the connector pipe 31 of the suction channel 3, and opens the connector pipe 29, so that the flushing fluid is fed from the flushing connector 13, through the channels 25, 26 and 27, the part of the cylinder 16 behind the trailing end of the piston 15, and the connector pipe 29, to the flushing channel 4 in the suction and flushing shaft 2. In order to withdraw by suction, the flushing fluid fed in, it is merely necessary to release the spring loaded plunger 14, so that it is returned to said inoperative position together with the piston 15, under the action of the spring 21. The flushing fluid flowing through the flushing channel 4 is also fed briefly to the suction channel 3 during the return stroke of the piston 15 to said inoperative initial position, so that the flushing and cleansing operation described above is effectively completed.

In order to prevent egress of the flushing fluid from the switching valve 6, the valve casing 23 and the closure plate 24 are sealed in fluid-tight fashion by the sealing elements 28. The plunger 14 is sealed with respect to the closure plate 24 by means of a sealing ring 32. All other joints which might allow the flushing fluid to leak from the switching valve 6, are sealed by conventional sealing means (not shown).

The switching valve described above may be replaced by a rotary valve (not shown) having the same mode of operation.

Also, the action of the switching valve may be reversed, so that flushing fluid is continuously ducted into the bodily cavity in said inoperative valve position, whilst the flushing fluid as well as secretions and the like are not drawn off by suction until after the actuation of the valve. A detent element or the like may be provided in the handle, effectively to prevent accidental rotary displacement of the optical system in the handle.

The upper part of the handle comprising the finger holes separated from each other by a web, and the lower part of the handle accommodating the switching valve, may be in the form of individual releasably interconnectible components whereby the lower part can be combined with the upper part which may have any convenient shape.

What is claimed is:

1. An endoscope comprising a suction and flushing shaft provided with a suction and a flushing channel, a handle adapted to be coupled to said shaft and a switching valve accommodated in said handle and having switching positions for connecting the suction channel and the flushing channel to a suction sources and to a flushing fluid source, respectively, and for interrupting the connections of said channels to said sources, the switching valve having a further switching position for connecting said suction channel to said flushing fluid source.

2. An endoscope as claimed in claim 1, wherein the switching valve comprises means for interrupting the connection between the flushing channel and the source of flushing fluid and the connection between the suction channel and the suction source during the connection of the suction channel to the flushing fluid source.

3. An endoscope as claimed in claim 1, wherein the switching valve has an inoperative switching position for connecting the suction channel to the suction source and for shutting off the flushing channel from the flushing fluid source.

4. An endoscope as claimed in claim 3, wherein a spring is provided for retaining the switching valve in said inoperative switching position.

5. An endoscope as claimed in claim 1, wherein the switching valve has a switched through position for connecting the flushing channel to the flushing fluid source and for shutting off the suction channel from the suction source.

6. An endoscope as claimed in claim 1, comprising detent means defining said further switching position and a spring for overriding said detent means.

7. An endoscope as claimed in claim 1, wherein the handle is formed with at least two holes separated from one another by a web, at least one of the holes being dimensioned to receive a finger.

8. An endoscope as claimed in claim 7, wherein said handle has an upper and a lower part which are releasably attachable to one another, said holes being formed in said upper part and said lower part accommodating the switching valve, and said upper part of any convenient shape.

9. An endoscope comprising a suction and flushing shaft provided with a suction channel and a flushing channel, a handle adapted to be coupled to said shaft and a switching valve accommodated in said handle, said switching valve having three switching positions with a first of the three switching positions connecting the suction channel to a suction source and disconnecting the flushing channel from a flushing fluid source, a second position of said three switching positions blocking said suction source and connecting the suction channel to the flushing fluid source, and a third position of the three switching positions connecting the flushing source to the flushing channel and blocking flow to the suction channel and from the suction source.

10. An endoscope according to claim 9, wherein said switching valve has spring means biasing the valve to the first position.

* * * * *